(12) United States Patent
He et al.

(10) Patent No.: US 10,702,557 B2
(45) Date of Patent: Jul. 7, 2020

(54) COMBINED EXTERNAL MEDICINE FOR TREATING PROSTATE DISEASES

(71) Applicant: Shaanxi Jianhua Biopharmaceutical Co., Ltd., Shaanxi (CN)

(72) Inventors: Jian He, Shaanxi (CN); Hua Wang, Shaanxi (CN)

(73) Assignee: Shaanxi Jianhua Biopharmaceutical Co., Ltd., Shaanxi (CN)

( * ) Notice: Subject to any disclaimer, the term of this patent is extended or adjusted under 35 U.S.C. 154(b) by 0 days.

(21) Appl. No.: 16/198,870

(22) Filed: Nov. 22, 2018

(65) Prior Publication Data

US 2019/0091267 A1    Mar. 28, 2019

Related U.S. Application Data

(63) Continuation of application No. PCT/CN2018/081059, filed on Mar. 29, 2018, and a continuation of application No. PCT/CN2016/083266, filed on May 25, 2016.

(30) Foreign Application Priority Data

May 19, 2017    (CN) .......................... 2017 1 0357637

(51) Int. Cl.

| A61K 36/00 | (2006.01) |
|---|---|
| A61K 35/57 | (2015.01) |
| A61K 35/62 | (2006.01) |
| A61K 36/8966 | (2006.01) |
| A61K 36/902 | (2006.01) |
| A61K 36/904 | (2006.01) |
| A61K 36/8969 | (2006.01) |
| A61K 36/9066 | (2006.01) |
| A61K 35/618 | (2015.01) |
| A61K 35/63 | (2015.01) |
| A61K 35/586 | (2015.01) |
| A61K 35/12 | (2015.01) |
| A61P 17/00 | (2006.01) |
| A61P 13/08 | (2006.01) |
| A61K 9/00 | (2006.01) |
| A61K 35/64 | (2015.01) |
| A61K 36/076 | (2006.01) |
| A61K 36/39 | (2006.01) |
| A61K 36/40 | (2006.01) |
| A61K 36/481 | (2006.01) |
| A61K 36/64 | (2006.01) |
| A61K 36/65 | (2006.01) |
| A61K 36/884 | (2006.01) |
| A61K 36/894 | (2006.01) |
| A61K 45/06 | (2006.01) |

(52) U.S. Cl.
CPC ............ *A61K 35/57* (2013.01); *A61K 9/0014* (2013.01); *A61K 35/12* (2013.01); *A61K 35/586* (2013.01); *A61K 35/618* (2013.01); *A61K 35/62* (2013.01); *A61K 35/63* (2015.01); *A61K 35/64* (2013.01); *A61K 36/076* (2013.01); *A61K 36/39* (2013.01); *A61K 36/40* (2013.01); *A61K 36/481* (2013.01); *A61K 36/64* (2013.01); *A61K 36/65* (2013.01); *A61K 36/884* (2013.01); *A61K 36/894* (2013.01); *A61K 36/8966* (2013.01); *A61K 36/8969* (2013.01); *A61K 36/902* (2013.01); *A61K 36/904* (2013.01); *A61K 36/9066* (2013.01); *A61K 45/06* (2013.01); *A61P 13/08* (2018.01); *A61P 17/00* (2018.01)

(58) Field of Classification Search
CPC ..................................................... A61K 36/00
See application file for complete search history.

(56) References Cited

FOREIGN PATENT DOCUMENTS

| CN | 101245140 | 8/2008 |
|---|---|---|
| CN | 103599535 | 2/2014 |
| CN | 105287638 | 2/2016 |
| CN | 107126443 | 9/2017 |
| WO | 2017201684 | 11/2017 |

OTHER PUBLICATIONS

Wang, Chunhui, "Medication Rules and Clinical Effect Observation of TCM External Treatment for Treating Breast Hyperplasia", Medicine & Public Health, China Master's Theses Full-Text Database, Dec. 15, 2015, pp. 6, 9-11 and 20-26.

Li, Lanqun, "TCM Syndromes and Types Distributing Features and Group Sequential Clinical Trail of Chronic Prostatitis", Medicine & Public Health, China Master's Theses Full-Text Database, Jun. 15, 2003, pp. 12-26.

Zheng et al., "Analysis on TCM syndromes and the rules for the prescription of herbal medicines for malignant pleural effusion", Beijing Journal of Traditional Chinese Medicine, Jul. 31, 2015, pp. 529-531.

(Continued)

*Primary Examiner* — Qiuwen Mi
(74) *Attorney, Agent, or Firm* — JCIPRNET

(57) ABSTRACT

The invention provides a combined external medicine for treating prostate diseases and a method using the same. The combined external medicine includes a pre-immune composition comprising multi-immune powder and a noble bottle tree decoction, a lesion active composition comprising the multi-immune powder and a first medical decoction prepared from a first Chinese medical composition for treating prostate diseases, and a double rib active composition comprising the multi-immune powder and a second medical decoction prepared from a second Chinese medical composition for conditioning liver and kidney. The method includes applying the pre-immune composition on skin of lesion part and skin of the left and right ribs; waiting for 5-10 minutes; applying the lesion active composition and the double rib active composition on the skin of the lesion part and skin of the left and right ribs; and airing for 10-40 minutes.

7 Claims, No Drawings

(56) References Cited

OTHER PUBLICATIONS

Wang, Tao: "Study on Syndrome Differentiation and Treatment of Liuwei Dihuang Pill and Its Associated Prescriptions by Statistical Analysis on Medical Records", Medicine & Public Health, China Doctoral Dissertations Full-Text Database, Jun. 15, 2011, pp. 34 and 84.
Jin et al., "Treatment of 68 Cases of Chronic Prostatitis with Syndrome Differentiation and Western Medicine", Shaanxi Traditional Chinese Medicine, Dec. 31, 2013, pp. 1602-1603.
Fan, Xuezhong, "Treatment of 217 Cases of Benign Prostatic Hyperplasia by Resolving Hard Lumps, Dispersing Blood Stasis, Descending the Turbid, Clearing Heat and Removing Dampness", Journal of New Chinese Medicine, Dec. 31, 1999, pp. 26-27.
"International Search Report (Form PCT/ISA/210) of PCT/CN2018/081059", dated Jul. 6, 2018, with English translation thereof, pp. 1-14.
"Written Opinion (Form PCT/ISA/237) of PCT/CN2018/081059", dated Jul. 6, 2018, with English translation thereof, pp. 1-11.
"International Search Report (Form PCT/ISA/210) of PCT/CN2016/083266", dated Feb. 8, 2017, with English translation thereof, pp. 1-8.
"Written Opinion (Form PCT/ISA/237) of PCT/CN2016/083266", dated Feb. 8, 2017, with English translation thereof, pp. 1-12.
"Office Action of China Counterpart Application No. 201710357637X," dated Nov. 17, 2017, with English translation thereof, pp. 1-5.
"Office Action of China Counterpart Application No. 201710357637X," dated Jan. 11, 2018, with English translation thereof, pp. 1-2.

COMBINED EXTERNAL MEDICINE FOR TREATING PROSTATE DISEASES

CROSS-REFERENCE TO RELATED APPLICATION

This application is a continuation of international PCT application Ser. No. PCT/CN2016/083266, filed on May 25, 2016, and international PCT application Ser. No. PCT/CN2018/081059, filed on Mar. 29, 2018, which claims the priority benefit of China application no. 201710357637.X, filed on May 19, 2017. The entirety of each of the above-mentioned patent applications is hereby incorporated by reference herein and made a part of this specification.

BACKGROUND

1. Field of the Invention

Accordingly, the present invention belongs to the field of pharmaceutical preparations containing antibodies, and in particular relates to a combined external medicine for treating prostate diseases.

2. Description of Related Art

The i26 immune egg powder is produced in the United States, is a nutrient sold in a food form in China, and is egg powder refined from whole eggs. Hens that produce these eggs have been in the environment containing 26 kinds or more of inactivated bacteria for a long time. The hens produce antibodies and a variety of low molecular complex factors that support immune responses when being stimulated by various pathogens.

The i26 immune egg powder preserves the immune factors in hyperimmune eggs, and is rich in immunoglobulin Igy and ovalbumin. The naturally occurring immune components of this egg powder, whether specific or non-specific, can be absorbed by the human body through passive transportation and other methods. The small biologically active components of immunoglobulin can function systematically, and the biological factors contained therein can work together to adjust the human body immune response, especially inflammation caused by autoimmune responses and irritating responses, and the like, so as to help the human body maintain immune dynamic equilibrium and improve health. The i26 immune egg powder is the world's most advanced and unique scientifically proven purely natural product that can be orally administrated to directly provide desired antibodies and immune co-factors to human to protect against bacteria and viruses.

In Chinese Patent 200810034553.3, an external ointment prepared by using i26 immune egg powder and a traditional Chinese medical decoction can be applied to a lesion and its nearby skin. By using the strong penetration to the skin after the i26 immune egg powder is combined with traditional Chinese medicine ingredients to undergo a chemical reaction, the pharmaceutical ingredients of the traditional Chinese medical decoction directly act on the affected part of the human body, and then circulate to the whole body. The characteristics are that the effect is fast, the use amount of the medicine is reduced, the medicine directly reaches the lesion, and there are no side effects. For example, for mastitis or hyperplasia of mammary gland, the ointment is applied to the skin near a breast lesion; for prostatitis or prostatic hyperplasia, etc., the ointment is applied to lesion parts such as perineum; for pleurisy or pleural effusion, the ointment is applied to lesion parts such as double back. However, patients suffering from the above diseases often have liver and kidney deficiency, especially frail patients such as the elderly and children. According to the principle of addressing the root causes of traditional Chinese medicine, the whole conditioning will be carried out from the internal organs, so some pharmaceutical ingredients for whole conditioning, such as medicines for conditioning liver and kidney, are often added to original pharmaceutical ingredients for treating diseases, but these conditioning medicines are less specific, and will often produce antagonistic side effects when being used with the original medicines for treating diseases to affect the therapeutic effect.

The international application (PCT/CN2016/083266) discloses a combined external medicine consisting of a lesion active composition and a double rib active composition. The two active ingredients are respectively used at different parts to avoid negative effects caused by medicine offset, thereby speeding up the treatment of disease. Specifically, a combined external medicine for treating prostatitis is also disclosed. Although the combined medicine has a relatively good effect in a treatment process, and a high total effective rate, the cure rate is still not high enough, and the medicine needs to be continuously used for a non-cured but markedly effective patient, so that the treatment time is relatively increased. Therefore, it is of great significance to improve the cure rate of the combined external medicine and shortening the treatment time.

SUMMARY

The present invention is directed to a combined external medicine for treating prostate diseases, which can improve the cure rate and shorten the treatment time.

The combined external medicine for treating prostate diseases comprises a pre-immune composition comprising multi-immune powder and a noble bottle tree decoction, a lesion active composition comprising the multi-immune powder and a first medical decoction prepared from a first Chinese medical composition for treating prostate diseases, and a double rib active composition comprising the multi-immune powder and a second medical decoction prepared from a second Chinese medical composition for conditioning liver and kidney.

Preferably, the multi-immune powder is i26 immune egg powder.

The pre-immune composition is used prior to the lesion active composition and the double rib active composition.

The lesion active composition is used for a lesion, and the double rib active composition is used for left and right ribs.

The prostate diseases that can be treated by the combined external medicine include but not limited to prostatitis and prostatic hyperplasia and hypertrophy.

The multi-immune powder is an active substance containing a variety of immune factors. When being simultaneously injected with a variety of (20 or more) specific inactivated bacterial antigens, poultry will activate their immune systems, and produce corresponding various antibodies and various immune factors. These antibodies and immune factors are concentrated in eggs laid by the poultry, and the eggs are turned into powder by low-temperature drying to obtain the multi-immune powder. Preferably, the poultry are chickens, ducks, geese or quails. More preferably, the poultry are chickens.

The i26 immune egg powder containing a variety of antibodies and cellular immune factors is combined with a therapeutic traditional Chinese medicine for treating corresponding disease are prepared into an ointment to be applied to skin, and has strong skin penetration effect after undergoing a chemical reaction to take effect. Through experiments, it is found that not only the i26 immune egg powder, but also multi-immune powder produced by other poultry through a production process of i26 immune egg powder also can achieve the same effect. The multi-immune powder contains a variety of cellular immune factors, and is combined with the therapeutic traditional Chinese medicine for the corresponding disease to be applied to the skin of the human body; active ingredients in the multi-immune egg powder carry the medicine to permeate the cells in the skin and blood to participate in the internal circulation, thereby playing a therapeutic effect to achieve the treatment purpose.

For example: the poultry are placed in a quiet pollution-free environment, and when the spawning poultry are stimulated by various (20 or more) inactivated bacterial pathogen multivalent mixtures for multiple times, the poultry will inevitably activate their immune systems to produce a variety of specific immunoglobulins and a variety of cellular immune factors and the like, and deliver these multiple antibodies produced in vivo to eggs in one effort. These eggs are prepared into powder by a low temperature drying technique to obtain the multi-immune powder of the present invention.

The "first Chinese medical composition for treating prostate diseases" refers to a traditional Chinese medicine or traditional Chinese medicine composition that should be used for treating prostate diseases as known in the prior art.

The "second Chinese medical composition for conditioning liver and kidney" refers to a traditional Chinese medicine or traditional Chinese medicine composition for conditioning or increasing liver and kidney functions as known in the prior art. For example, the traditional Chinese medicine for treating kidney yin deficiency includes but not limited to radix rehmanniae, fructus corni, rhizoma dioscoreae, cortex moutan, poria cocos, rhizoma alismatis, rhizoma polygonati and the like; the traditional Chinese medicine for treating fire hyperactivity due to kidney yin deficiency includes but not limited to cortex phellodendri, rhizoma anemarrhenae, radix rehmanniae, fructus corni, rhizoma dioscoreae, cortex moutan, poria cocos, rhizoma alismatis and the like; the traditional Chinese medicine for treating kidney yang deficiency includes but not limited to rehmanniae vaporata, fructus corni, rhizoma dioscoreae, cortex moutan, poria cocos, rhizoma alismatis and the like.

In the combined external medicine for treating prostate diseases, the second Chinese medical composition for conditioning liver and kidney includes the following ingredients. When kidney yin deficiency is conditioned, the second Chinese medical composition comprises 15-30 parts by weight of radix rehmanniae, 15-30 parts by weight of rehmanniae vaporata, or 15-30 parts by weight of a mixture of radix rehmanniae and rehmanniae vaporata in a weight ratio of 1:1; 10-20 parts by weight of fructus corni; 15-30 parts by weight of rhizoma dioscoreae; 6-12 parts by weight of cortex moutan; 6-12 parts by weight of poria cocos; 6-12 parts by weight of rhizoma alismatis; 10-20 parts by weight of cuscuta chinensis lam; 10-20 parts by weight of semen astragali complanati; and 10-20 parts by weight of rhizoma polygonati. When fire hyperactivity due to kidney yin deficiency is conditioned, the second Chinese medical composition comprises 15-30 parts by weight of radix rehmanniae, 15-30 parts by weight of rehmanniae vaporata, or 15-30 parts by weight of a mixture of radix rehmanniae and rehmanniae vaporata in a weight ratio of 1:1; 10-20 parts by weight of fructus corni; 15-30 parts by weight of rhizoma dioscoreae; 6-12 parts by weight of cortex moutan; 6-12 parts by weight of poria cocos; 6-12 parts by weight of rhizoma alismatis; 15-30 parts by weight of rhizoma anemarrhenae; and 15-30 parts by weight of cortex phellodendri. When kidney yang deficiency is conditioned, the second Chinese medical composition comprises 15-30 parts by weight of radix rehmanniae, 15-30 parts by weight of rehmanniae vaporata, or 15-30 parts by weight of a mixture of radix rehmanniae and rehmanniae vaporata in a weight ratio of 1:1; 10-20 parts by weight of fructus corni; 15-30 parts by weight of rhizoma dioscoreae; 6-12 parts by weight of cortex moutan; 6-12 parts by weight of poria cocos; 6-12 parts by weight of rhizoma alismatis; 10-20 parts by weight of rhizoma polygonati; 10-20 parts by weight of morindae officinalis; 10-30 parts by weight of herba epimedii; 10-30 parts by weight of cortex cinnamomi; and 10-30 parts by weight of radix paeoniae alba.

When the combined external medicine for treating prostate diseases is used for treating prostatitis, the first Chinese medical composition for treating prostatitis comprises 15-30 parts by weight of leech; 20-40 parts by weight of earthworm; 15-30 parts by weight of eupolyphaga; 20-50 parts by weight of fructus foeniculi; 20-40 parts by weight of concha ostreae; 10-20 parts by weight of pangolin scales; 20-40 parts by weight of carapax trionycis; 15-30 parts by weight of radix achyranthis bidentatae; 20-40 parts by weight of rhizoma sparganii; 20-40 parts by weight of rhizoma curcumae; 15-30 parts by weight of radix notoginseng; 20-40 parts by weight of litchi core; 20-60 parts by weight of caulis spatholobi; 20-40 parts by weight of chinese honeylocust spine; 20-40 parts by weight of dandelion; 15-30 parts by weight of myrrh; 15-30 parts by weight of frankincense; 15-30 parts by weight of acacia catechu; 20-40 parts by weight of semen plantaginis; 20-40 parts by weight of hedyotis diffusa; 20-40 parts by weight of tangerine seed; 20-40 parts by weight of cyrtomium fortunei; 15-30 parts by weight of rhizoma chuanxiong; and 15-30 parts by weight of prunella vulgaris.

When the combined external medicine for treating prostate diseases is used for treating prostatic hyperplasia and hypertrophy, the first Chinese medical composition for treating prostatic hyperplasia and hypertrophy comprises 10-30 parts by weight of cortex phellodendri; 10-30 parts by weight of rhizoma anemarrhenae; 5-15 parts by weight of pangolin scales; 10-20 parts by weight of carapax trionycis; 10-30 parts by weight of concha ostreae; 10-30 parts by weight of radix achyranthis bidentatae; 20-50 parts by weight of lysimachia christinae hance; 10-30 parts by weight of fructus crataegi; 10-30 parts by weight of rhizoma curcumae; 10-30 parts by weight of semen plantaginis; 10-40 parts by weight of caulis spatholobi; 20-40 parts by weight of herba leonuri; 10-30 parts by weight of rheum officinale; 10-30 parts by weight of chinese honeylocust spine; 10-30 parts by weight of acacia catechu; 10-30 parts by weight of leech; 10-30 parts by weight of lumbricus; 10-30 parts by weight of eupolyphaga; 15-50 parts by weight of largehead atractylodes rhizome; 10-30 parts by weight of rhizoma chuanxiong; and 10-30 parts by weight of prunella vulgaris.

In the combined external medicine for treating prostate diseases provided by the present invention, the weight ratios of the i26 immune egg powder to the noble bottle tree decoction, the first Chinese medical composition for treating prostate diseases or the second Chinese medical composition for conditioning liver and kidney are 25-45:65-75; preferably 30-40:60-70; more preferably 38:62.

The combined external medicine for treating prostate diseases provided by the present invention can be prepared by any existed methods, for example:

1) the noble bottle tree, the first Chinese medical composition for treating prostate diseases, and the second Chinese medical composition for conditioning liver and kidney are respectively prepared;

2) the above three kinds of medicines are respectively decocted for 40-50 minutes into decoctions, and then concentrated over a high heat to a suitable amount, and cooled to 0° C. to 30° C. to obtain a noble bottle tree decoction, a first medical decoction for treating prostatis, and a second medical decoction for conditioning liver and kidney;

3) the noble bottle tree decoction, the first medical decoction for treating prostatis, and second medical decoction for conditioning liver and kidney are respectively mixed with the multi-immune powder according to a weight ratio to obtain the pre-immune composition, the lesion active composition, and the double rib active composition.

An application method of the combined external medicine for treating prostate diseases provided by the present invention is as follows:

The combined external medicine is applied to skin, and the application part is washed with water before applying; after air-drying, the pre-immune composition is respectively applied to skin of the lesion part and skin of left and right ribs; 5-10 minutes later, the lesion active composition and the double rib active composition are respectively applied to the skin of the lesion part and the skin of the left and right ribs; after applying, airing for 10-40 minutes is needed, and the medicine is applied twice a day, once in the morning and once in the evening. The lesion part is the skin of perineum, testis skin or the like.

The present invention has the following advantages that:

1. The combined external medicine for treating prostate diseases provided by the invention has a high cure rate and short cure time, and the cure rate can reach 86% or more when the medicine is applied for 10 days. Since the multi-immune powder itself has the function of regulating the body's immune system, the multi-immune powder combined with the traditional Chinese medical composition can enhance the efficacy of the traditional Chinese medical composition, the medical composition applied to the lesion and the medical composition applied to the double ribs simultaneously play a role, and the two can coordinate with each other to speed up the disease treatment, shorten the course of treatment, and improve the cure rate. The noble bottle tree can harmonize stomach and prompt digestion and enhance the function of intestines. When the medicine is used, the pre-immune composition comprising the noble bottle tree decoction and the multi-immune powder is firstly applied, thereby improving the cure rate and shortening the cure time.

2. The lesion active composition and the double rib active composition are respectively applied to the lesion and the left and right ribs, which improves the specificity of pharmaceutical ingredients, and avoids the medicine offset phenomenon. The combined external medicine is applied to the skin, the pharmaceutical ingredients directly enter cells and blood, and the dosage is reduced, which is one-third or even one-fifth of the amount of an oral administration.

3. There are no side effects, and skin allergy will not be caused. The multi-immune powder is an active ingredient extracted from animal tissues, has the same identity to the human body, has an anti-inflammatory effect itself, is non-irritating to the skin, and can be used for a long time. There is no skin problem in the clinical use for two consecutive years. At the same time, the combined external medicine does not hurt the spleen, stomach, liver and kidney, and can achieve the purpose of effectively treating diseases without taking injections and taking medicines.

4. The medicine is convenient to use. For some people, such as the elderly and critically ill patients, who inconveniently get up and open the mouth to take the medicine, the combined external medicine can be directly applied to skin to achieve the purpose of easy and fast treatment.

DESCRIPTION OF THE EMBODIMENTS

I. Combined External Medicine for Treating Prostatitis

Example 1 (Kidney Yin Deficiency)

1. Preparation of Combined External Medicine:

1) Preparation of Traditional Chinese Medicinal Materials:

Preparation of 100 g of noble bottle tree (*Sterculia nobilis*);

Preparation of therapeutic traditional Chinese medicinal materials for prostatitis: 15 g of leech, 20 g of lumbricus, 15 g of eupolyphaga, 20 g of fructus foeniculi, 20 g of concha ostreae, 10 g of pangolin scales, 20 g of carapax trionycis, 15 g of radix achyranthis bidentatae, 20 g of rhizoma sparganii, 20 g of rhizoma curcumae, 15 g of radix notoginseng, 20 g of litchi chinensis sonn, 20 g of caulis spatholobi, 20 g of chinese honeylocust spine, 20 g of dandelion, 15 g of myrrh, 15 g of frankincense, 15 g of acacia catechu, 20 g of semen plantaginis, 20 g of hedyotis diffusa, 20 g of tangerine seed, 20 g of cyrtomium fortunei, 15 g of rhizoma chuanxiong, and 15 g of prunella vulgaris.

Preparation of traditional Chinese medicinal materials for conditioning kidney yin deficiency: 15 g of radix rehmanniae, 10 g of fructus corni, 15 g of rhizoma dioscoreae, 6 g of cortex moutan, 6 g of poria cocos, 6 g of rhizoma alismatis, 10 g of cuscuta chinensis lam, 10 g of semen astragali complanati and 10 g of rhizoma polygonati.

2) The above three kinds of medicinal materials were decocted for 40-50 minutes into a decoction, and then concentrated over a high heat to a suitable amount, and cooled to 0° C. to 30° C. to obtain a noble bottle tree decoction, a first medical decoction for treating prostatis, and a second medical decoction for conditioning liver and kidney;

3) the noble bottle tree decoction, the first medical decoction for treating prostatis, and the second medical decoction for conditioning liver and kidney were respectively mixed with multi-immune powder according to a weight ratio of 38:62 to obtain a pre-immune composition, a lesion active composition, and a double rib active composition.

Example 2 (Kidney Yin Deficiency)

Preparation of traditional Chinese medicinal materials for conditioning kidney yin deficiency: 15 g of rehmanniae vaporata, 10 g of fructus corni, 15 g of rhizoma dioscoreae, 6 g of cortex moutan, 6 g of poria cocos, 6 g of rhizoma alismatis, 10 g of cuscuta chinensis lam, 10 g of semen astragali complanati and 10 g of rhizoma polygonati.

Others are the same as in Example 1.

Example 3 (Kidney Yin Deficiency)

Preparation of traditional Chinese medicinal materials for conditioning kidney yin deficiency: 15 g of radix rehmanniae, 15 g of rehmanniae vaporata, 10 g of fructus corni, 15 g of rhizoma dioscoreae, 6 g of cortex moutan, 6 g of poria cocos, 6 g of rhizoma alismatis, 10 g of cuscuta chinensis lam, 10 g of semen astragali complanati and 10 g of rhizoma polygonati.

Others are the same as in Example 1.

Example 4 (Fire Hyperactivity Due to Kidney Yin Deficiency)

Preparation of therapeutic traditional Chinese medicinal materials for prostatitis: 30 g of leech, 40 g of lumbricus, 30 g of eupolyphaga, 50 g of fructus foeniculi, 40 g of concha ostreae, 20 g of pangolin scales, 40 g of carapax trionycis, 30 g of radix achyranthis bidentatae, 40 g of rhizoma sparganii, 40 g of rhizoma curcumae, 30 g of radix notoginseng, 40 g of litchi chinensis sonn, 60 g of caulis spatholobi, 40 g of chinese honeylocust spine, 40 g of dandelion, 30 g of myrrh, 30 g of frankincense, 30 g of acacia catechu, 40 g of semen plantaginis, 40 g of hedyotis diffusa, 40 g of tangerine seed, 40 g of cyrtomium fortunei, 30 g of rhizoma chuanxiong, and 30 g of prunella vulgaris.

Preparation of traditional Chinese medicinal materials for conditioning fire hyperactivity due to kidney yin deficiency: 15 g of radix rehmanniae, 10 g of fructus corni, 15 g of rhizoma dioscoreae, 6 g of cortex moutan, 6 g of poria cocos, 6 g of rhizoma alismatis, 15 g of rhizoma anemarrhenae and 15 g of cortex phellodendri.

Others are the same as in Example 1.

Example 5 (Fire Hyperactivity Due to Kidney Yin Deficiency)

Preparation of traditional Chinese medicinal materials for conditioning fire hyperactivity due to kidney yin deficiency: 15 g of rehmanniae vaporata, 10 g of fructus corni, 15 g of rhizoma dioscoreae, 6 g of cortex moutan, 6 g of poria cocos, 6 g of rhizoma alismatis, 15 g of rhizoma anemarrhenae and 15 g of cortex phellodendri.

Others are the same as in Example 4.

Example 6 (Fire Hyperactivity Due to Kidney Yin Deficiency)

Preparation of traditional Chinese medicinal materials for conditioning fire hyperactivity due to kidney yin deficiency: 15 g of radix rehmanniae, 15 g of rehmanniae vaporata, 10 g of fructus corni, 15 g of rhizoma dioscoreae, 6 g of cortex moutan, 6 g of poria cocos, 6 g of rhizoma alismatis, 15 g of rhizoma anemarrhenae and 15 g of cortex phellodendri.

Others are the same as in Example 4.

Example 7 (Kidney Yang Deficiency)

Preparation of therapeutic traditional Chinese medicinal materials for prostatitis: 18 g of leech, 25 g of lumbricus, 23 g of eupolyphaga, 27 g of fructus foeniculi, 32 g of concha ostreae, 14 g of pangolin scales, 31 g of carapax trionycis, 22 g of radix achyranthis bidentatae, 34 g of rhizoma sparganii, 29 g of rhizoma curcumae, 23 g of radix notoginseng, 30 g of litchi chinensis sonn, 35 g of caulis spatholobi, 30 g of chinese honeylocust spine, 30 g of dandelion, 19 g of myrrh, 21 g of frankincense, 24 g of acacia catechu, 31 g of semen plantaginis, 30 g of hedyotis diffusa, 30 g of tangerine seed, 30 g of cyrtomium fortunei, 25 g of rhizoma chuanxiong, and 25 g of prunella vulgaris.

Preparation of traditional Chinese medicinal materials for conditioning kidney yang deficiency: 15 g of radix rehmanniae, 10 g of fructus corni, 15 g of rhizoma dioscoreae, 6 g of cortex moutan, 6 g of poria cocos, 6 g of rhizoma alismatis, 10 g of rhizoma polygonati, 10 g of morindae officinalis, 10 g of herba epimedii, 10 g of cortex cinnamomi and 10 g of radix paeoniae alba.

Others are the same as in Example 1.

Example 8 (Kidney Yang Deficiency)

Preparation of traditional Chinese medicinal materials for conditioning kidney yang deficiency: 15 g of rehmanniae vaporata, 10 g of fructus corni, 15 g of rhizoma dioscoreae, 6 g of cortex moutan, 6 g of poria cocos, 6 g of rhizoma alismatis, 10 g of rhizoma polygonati, 10 g of morindae officinalis, 10 g of herba epimedii, 10 g of cortex cinnamomi and 10 g of radix paeoniae alba.

Others are the same as in Example 7.

Example 9 (Kidney Yang Deficiency)

Preparation of traditional Chinese medicinal materials for conditioning kidney yang deficiency: 15 g of radix rehmanniae, 15 g of rehmanniae vaporata, 10 g of fructus corni, 15 g of rhizoma dioscoreae, 6 g of cortex moutan, 6 g of poria cocos, 6 g of rhizoma alismatis, 10 g of rhizoma polygonati, 10 g of morindae officinalis, 10 g of herba epimedii, 10 g of cortex cinnamomi and 10 g of radix paeoniae alba.

Others are the same as in Example 7.

The composition of combined external medicine for treating prostatitis prepared in the above Examples was applied as follows.

A total of 900 patients suffering from prostatitis were selected and averagely divided into 9 groups, and each group has 100 people. In each group, there were an elderly group having 50 people (over 65 years old) and an adult group having 50 people (16-65 years old). The prevalence rate of children was extremely low, so no children were selected.

The combined external medicine prepared in each Example was applied to skin. Before applying the medicine, an application part was washed with clear water. After air-drying, the pre-immune composition was respectively applied to skin of the lesion part and skin of left and right ribs. 5-10 minutes later, the lesion active composition and the double rib active composition were respectively applied to the skin of the lesion part and the skin of the left and right ribs. Airing for 10-40 minutes is needed after the application, and the medicine was applied twice a day, once in the morning and once in the evening. The lesion part is the skin of perineum, testis and the like. The medicine was applied for 10 days.

Treatment results were shown in Table 1.

TABLE 1

Treatment results of combined external medicine for treating prostatitis provided by Examples 1-9 of the present invention

| | | Elderly group (50 people) | | | | Adult group (50 people) | | | |
|---|---|---|---|---|---|---|---|---|---|
| | | Cured (number of people) | Effective (number of people) | Ineffective (number of people) | Cure rate (%) | Cured (number of people) | Effective (number of people) | Ineffective (number of people) | Cure rate (%) |
| Example 1 | Kidney yin deficiency | 44 | 6 | 0 | 88 | 43 | 7 | 0 | 86 |
| Example 2 | Kidney yin deficiency | 45 | 5 | 0 | 90 | 44 | 6 | 0 | 88 |
| Example 3 | Kidney yin deficiency | 44 | 6 | 0 | 88 | 45 | 5 | 0 | 90 |
| Example 4 | Fire hyperactivity due to kidney yin deficiency | 43 | 7 | 0 | 86 | 44 | 6 | 0 | 88 |
| Example 5 | Fire hyperactivity due to kidney yin deficiency | 45 | 5 | 0 | 90 | 43 | 7 | 0 | 86 |
| Example 6 | Fire hyperactivity due to kidney yin deficiency | 43 | 7 | 0 | 86 | 44 | 6 | 0 | 88 |
| Example 7 | Kidney yang deficiency | 45 | 5 | 0 | 90 | 45 | 5 | 0 | 90 |
| Example 8 | Kidney yang deficiency | 44 | 6 | 0 | 88 | 43 | 7 | 0 | 86 |
| Example 9 | Kidney yang deficiency | 45 | 5 | 0 | 90 | 44 | 6 | 0 | 88 |

In the second Embodiment (Examples 10-18) in the international application (PCT/CN2016/083266) was taken as a Control Example, the treatment results of the second Embodiment (Examples 10-18) in the international application (PCT/CN2016/083266) were shown in Table 2, and the treatment period was 2 weeks, wherein Examples 10-18 in the second Embodiment were sequentially and correspondingly taken as Control Examples 1-9, i.e., the control example 1 was the original Example 10, and so on.

TABLE 2

Treatment results of the combined external medicine for treating prostatitis provided by Control Examples

| | | Elderly group (50 people) | | | | Adult group (50 people) | | | |
|---|---|---|---|---|---|---|---|---|---|
| | | Cured (number of people) | Effective (number of people) | Ineffective (number of people) | Cure rate (%) | Cured (number of people) | Effective (number of people) | Ineffective (number of people) | Cure rate (%) |
| Control example 1 | Kidney yin deficiency | 30 | 20 | 0 | 60 | 41 | 90 | 0 | 82 |
| Control example 2 | Kidney yin deficiency | 32 | 17 | 1 | 64 | 40 | 10 | 0 | 80 |
| Control example 3 | Kidney yin deficiency | 34 | 15 | 1 | 68 | 38 | 10 | 2 | 76 |
| Control example 4 | Fire hyperactivity due to kidney yin deficiency | 35 | 15 | 0 | 70 | 40 | 9 | 1 | 80 |
| Control example 5 | Fire hyperactivity due to kidney yin deficiency | 36 | 12 | 2 | 72 | 40 | 10 | 0 | 80 |
| Control example 6 | Fire hyperactivity due to kidney yin deficiency | 35 | 14 | 1 | 70 | 41 | 9 | 0 | 82 |
| Control example 7 | Kidney yang deficiency | 32 | 17 | 1 | 64 | 39 | 11 | 0 | 78 |

TABLE 2-continued

Treatment results of the combined external medicine for treating prostatitis provided by Control Examples

| | | Elderly group (50 people) | | | | Adult group (50 people) | | | |
|---|---|---|---|---|---|---|---|---|---|
| | | Cured (number of people) | Effective (number of people) | Ineffective (number of people) | Cure rate (%) | Cured (number of people) | Effective (number of people) | Ineffective (number of people) | Cure rate (%) |
| Control example 8 | Kidney yang deficiency | 35 | 15 | 0 | 70 | 38 | 11 | 1 | 78 |
| Control example 9 | Kidney yang deficiency | 34 | 16 | 0 | 68 | 37 | 12 | 1 | 74 |

As can be seen from the comparison between Table 1 and Table 2, the combined external medicine for treating prostatitis provided by the present invention has a short treatment period and an improved cure rate, and the cure rate can reach 86% or more within 10 days.

II. Combined External Medicine for Treating Prostatic Hyperplasia and Hypertrophy Example 10 (Kidney Yin Deficiency)

1. Preparation of combined external medicine
1) Preparation of traditional Chinese medicinal materials
Preparation of 100 g of noble bottle tree;
Preparation of therapeutic traditional Chinese medicinal materials for prostatic hyperplasia and hypertrophy: 10 g of cortex phellodendri, 10 g of rhizoma anemarrhenae, g of pangolin scales, 10 g of carapax trionycis, 10 g of concha ostreae, 10 g of radix achyranthis bidentatae, 20 g of lysimachia christinae hance, 10 g of fructus crataegi, 10 g of rhizoma curcumae, 10 g of semen plantaginis, 10 g of caulis spatholobi, 20 g of herba leonuri, 10 g of rheum officinale, 10 g of chinese honeylocust spine, 10 g of acacia catechu, 10 g of leech, 10 g of lumbricus, 10 g of eupolyphaga, 15 g of largehead atractylodes rhizome, 10 g of rhizoma chuanxiong and 10 g of prunella vulgaris.

Preparation of traditional Chinese medicinal materials for conditioning kidney yin deficiency: 15 g of radix rehmanniae, 10 g of fructus corni, 15 g of rhizoma dioscoreae, 6 g of cortex moutan, 6 g of poria cocos, 6 g of rhizoma alismatis, 10 g of cuscuta chinensis lam, 10 g of semen astragali complanati and 10 g of rhizoma polygonati.

2) The above three kinds of medicinal materials were respectively decocted for 40-50 minutes into decoctions, and then concentrated over a high heat to a suitable amount, and cooled to 0° C. to 30° C. to obtain a noble bottle tree decoction, a first medical decoction for treating prostatic hyperplasia and hypertrophy, and a second medical decoction for conditioning liver and kidney;

3) the noble bottle tree decoction, the first medical decoction for treating prostatic hyperplasia and hypertrophy, and the second medical decoction for conditioning liver and kidney were respectively mixed with multi-immune powder according to a weight ratio of 38:62 to obtain a pre-immune composition, a lesion active composition, and a double rib active composition.

Example 11 (Kidney Yin Deficiency)

Preparation of traditional Chinese medicinal materials for conditioning kidney yin deficiency: 15 g of rehmanniae vaporata, 15 g of rhizoma dioscoreae, 6 g of cortex moutan, 6 g of poria cocos, 6 g of rhizoma alismatis, 10 g of cuscuta chinensis lam, 10 g of semen astragali complanati and 10 g of rhizoma polygonati.

Others are the same as in Example 10.

Example 12 (Kidney Yin Deficiency)

Preparation of traditional Chinese medicinal materials for conditioning kidney yin deficiency: 15 g of radix rehmanniae, 15 g of rehmanniae vaporata, 10 g of fructus corni, 15 g of rhizoma dioscoreae, 6 g of cortex moutan, 6 g of poria cocos, 6 g of rhizoma alismatis, 10 g of cuscuta chinensis lam, 10 g of semen astragali complanati and 10 g of rhizoma polygonati.

Others are the same as in Example 10.

Example 13 (Fire Hyperactivity Due to Kidney Yin Deficiency)

Preparation of therapeutic traditional Chinese medicinal materials for prostatic hyperplasia and hypertrophy: 30 g of cortex phellodendri, 30 g of rhizoma anemarrhenae, 15 g of pangolin scales, 20 g of carapax trionycis, 30 g of concha ostreae, 30 g of radix achyranthis bidentatae, 50 g of lysimachia christinae hance, 30 g of fructus crataegi, 30 g of rhizoma curcumae, 30 g of semen plantaginis, 40 g of caulis spatholobi, 40 g of herba leonuri, 30 g of rheum officinale, 30 g of chinese honeylocust spine, 30 g of acacia catechu, 30 g of leech, 30 g of lumbricus, 30 g of eupolyphaga, 50 g of largehead atractylodes rhizome, 30 g of rhizoma chuanxiong and 30 g of prunella vulgaris.

Preparation of traditional Chinese medicinal materials for conditioning fire hyperactivity due to kidney yin deficiency: 15 g of radix rehmanniae, 10 g of fructus corni, 15 g of rhizoma dioscoreae, 6 g of cortex moutan, 6 g of poria cocos, 6 g of rhizoma alismatis, 15 g of rhizoma anemarrhenae and 15 g of cortex phellodendri.

Others are the same as in Example 1.

Example 14 (Fire Hyperactivity Due to Kidney Yin Deficiency)

Preparation of traditional Chinese medicinal materials for conditioning fire hyperactivity due to kidney yin deficiency: 15 g of rehmanniae vaporata, 10 g of fructus corni, 15 g of rhizoma dioscoreae, 6 g of cortex moutan, 6 g of poria cocos, 6 g of rhizoma alismatis, 15 g of rhizoma anemarrhenae and 15 g of cortex phellodendri.

Others are the same as in Example 13.

Example 15 (Fire Hyperactivity Due to Kidney Yin Deficiency)

Preparation of traditional Chinese medicinal materials for conditioning fire hyperactivity due to kidney yin deficiency: 15 g of radix rehmanniae, 15 g of rehmanniae vaporata, 10 g of fructus corni, 15 g of rhizoma dioscoreae, 6 g of cortex moutan, 6 g of poria cocos, 6 g of rhizoma alismatis, 15 g of rhizoma anemarrhenae and 15 g of cortex phellodendri.
Others are the same as in Example 13.

Example 16 (Kidney Yang Deficiency)

Preparation of traditional Chinese medicinal materials for treating prostatic hyperplasia and hypertrophy: 14 g of cortex phellodendri, 19 g of rhizoma anemarrhenae, 5-15 g of pangolin scales, 15 g of carapax trionycis, 21 g of concha ostreae, 21 g of radix achyranthis bidentatae, 36 g of lysimachia christinae hance, 19 g of fructus crataegi, 20 g of rhizoma curcumae, 20 g of semen plantaginis, 27 g of caulis spatholobi, 31 g of herba leonuri, 22 g of rheum officinale, 16 g of chinese honeylocust spine, 17 g of acacia catechu, 15 g of leech, 18 g of lumbricus, 18 g of eupolyphaga, 35 g of largehead atractylodes rhizome, 20 g of rhizoma chuanxiong and 20 g of prunella vulgaris.
Preparation of therapeutic traditional Chinese medicinal materials for conditioning kidney yang deficiency: 15 g of radix rehmanniae, 10 g of fructus corni, 15 g of rhizoma dioscoreae, 6 g of cortex moutan, 6 g of poria cocos, 6 g of rhizoma alismatis, 10 g of rhizoma polygonati, 10 g of morindae officinalis, 10 g of herba epimedii, 10 g of cortex cinnamomi and 10 g of radix paeoniae alba.
Others are the same as in Example 1.

Example 17 (Kidney Yang Deficiency)

Preparation of traditional Chinese medicinal materials for conditioning kidney yang deficiency: 15 g of rehmanniae vaporata, 10 g of fructus corni, 15 g of rhizoma dioscoreae, 6 g of cortex moutan, 6 g of poria cocos, 6 g of rhizoma alismatis, 10 g of rhizoma polygonati, 10 g of morindae officinalis, 10 g of herba epimedii, 10 g of cortex cinnamomi and 10 g of radix paeoniae alba.
Others are the same as in Example 16.

Example 18 (Kidney Yang Deficiency)

Preparation of traditional Chinese medicinal materials for conditioning kidney yang deficiency: 15 g of radix rehmanniae, 15 g of rehmanniae vaporata, 10 g of fructus corni, 15 g of rhizoma dioscoreae, 6 g of cortex moutan, 6 g of poria cocos, 6 g of rhizoma alismatis, 10 g of rhizoma polygonati, 10 g of morindae officinalis, 10 g of herba epimedii, 10 g of cortex cinnamomi and 10 g of radix paeoniae alba.
Others are the same as in Example 16.

The combined external medicine for treating prostatic hyperplasia and hypertrophy prepared in the above Examples 10-18 was applied as follows.

A total of 900 patients suffering from prostatic hyperplasia were selected and averagely divided into 9 groups, each group having 100 people. In each group, there were an elderly group having 50 people (over 65 years old) and an adult group having 50 people (16-65 years old). The prevalence rate of children was extremely low, so no children were selected.

The combined external medicine prepared in each examples was applied to skin. Before applying the medicine, the application part was washed with clear water. After air-drying, a pre-immune composition was respectively applied to the skin of a lesion part and the skin of left and right ribs. 5-10 minutes later, a lesion active composition and a double rib active composition were respectively applied to the skin of the lesion part and the skin of the left and right ribs. Airing for 10-40 minutes is needed after application, and the medicine was applied twice a day, once in the morning and once in the evening. The lesion part was skin of perineum, testis and the like. The medicine was applied for 10 days.

Treatment results were shown in Table 3.

TABLE 3

Treatment results of combined external medicine for treating prostatic hyperplasia and hypertrophy provided by Examples 9-18 of the present invention.

| | | Elderly group (50 people) | | | | Adult group (50 people) | | | |
|---|---|---|---|---|---|---|---|---|---|
| | | Cured (number of people) | Effective (number of people) | Ineffective (number of people) | Cure rate (%) | Cured (number of people) | Effective (number of people) | Ineffective (number of people) | Cure rate (%) |
| Example 10 | Kidney yin deficiency | 43 | 7 | 0 | 86 | 45 | 5 | 0 | 90 |
| Example 11 | Kidney yin deficiency | 43 | 7 | 0 | 86 | 43 | 7 | 0 | 86 |
| Example 12 | Kidney yin deficiency | 45 | 5 | 0 | 90 | 44 | 6 | 0 | 88 |
| Example 13 | Fire hyperactivity due to kidney yin deficiency | 43 | 7 | 0 | 86 | 45 | 5 | 0 | 90 |
| Example 14 | Fire hyperactivity due to kidney yin deficiency | 45 | 5 | 0 | 90 | 44 | 6 | 0 | 88 |
| Example 15 | Fire excess due to kidney yin deficiency | 44 | 6 | 0 | 88 | 43 | 5 | 0 | 90 |
| Example 16 | Kidney yang deficiency | 43 | 7 | 0 | 86 | 43 | 5 | 0 | 90 |

TABLE 3-continued

Treatment results of combined external medicine for treating prostatic hyperplasia and hypertrophy provided by Examples 9-18 of the present invention.

|  |  | Elderly group (50 people) | | | | Adult group (50 people) | | | |
| --- | --- | --- | --- | --- | --- | --- | --- | --- | --- |
|  |  | Cured (number of people) | Effective (number of people) | Ineffective (number of people) | Cure rate (%) | Cured (number of people) | Effective (number of people) | Ineffective (number of people) | Cure rate (%) |
| Example 17 | Kidney yang deficiency | 44 | 6 | 0 | 88 | 45 | 5 | 0 | 90 |
| Example 18 | Kidney yang deficiency | 43 | 7 | 0 | 86 | 44 | 6 | 0 | 88 |

Control Examples

The pre-immune composition was not applied to the skin of the lesion site and the skin of left and right ribs, that is, the combined external medicine contains only the lesion active composition and the double rib active composition; the Examples 10-18 without the pre-immune composition were respectively and correspondingly taken as Control Examples 10-18. Others are the same as in Examples 10-18.

Application of the combined external medicine for treating prostatic hyperplasia prepared in the above Examples 10-18

A total of 900 patients suffering from prostatic hyperplasia were selected and divided into 9 groups, each group having 100 people. In each group, there were an elderly group having 50 people (over 65 years old) and an adult group having 50 people (16-65 years old). The prevalence rate of children was extremely low, so no children were selected.

The combined external medicine prepared in Control Examples 9-18 was applied to the skin. Before applying the medicine, the application site was washed with clear water. After air-drying, the lesion active composition and the double rib active composition were respectively applied to the skin of the lesion site and the skin of left and right ribs. It should be aired for 10-40 minutes after application, and the medicine was applied twice a day, once in the morning and once in the evening. The lesion was located at the skin of the perineum, testis and the like. The medicine was applied for two weeks.

The treatment results were shown in Table 4.

TABLE 4

Treatment results of combined external medicine for treating prostatic hyperplasia provided by Control Examples 10-18 (not containing the pre-immune composition)

|  |  | Elderly group (50 people) | | | | Adult group (50 people) | | | |
| --- | --- | --- | --- | --- | --- | --- | --- | --- | --- |
|  |  | Cure (number of people) | Effective (number of people) | Ineffective (number of people) | Cure rate (%) | Cure (number of people) | Effective (number of people) | Ineffective (number of people) | Cure rate (%) |
| Control example 10 | Kidney yin deficiency | 27 | 22 | 1 | 54 | 33 | 15 | 2 | 66 |
| Control example 11 | Kidney yin deficiency | 31 | 18 | 1 | 62 | 35 | 15 | 0 | 70 |
| Control example 12 | Kidney yin deficiency | 33 | 16 | 1 | 66 | 36 | 13 | 1 | 72 |
| Control example 13 | Fire hyperactivity due to kidney yin deficiency | 34 | 14 | 2 | 68 | 30 | 20 | 0 | 60 |
| Control example 14 | Fire hyperactivity due to kidney yin deficiency | 37 | 12 | 1 | 74 | 28 | 20 | 2 | 56 |
| Control example 15 | Fire hyperactivity due to kidney yin deficiency | 35 | 14 | 1 | 70 | 38 | 12 | 0 | 76 |
| Control example 16 | Kidney yang deficiency | 33 | 17 | 0 | 66 | 34 | 15 | 1 | 68 |
| Control example 17 | Kidney yang deficiency | 34 | 15 | 1 | 68 | 37 | 13 | 0 | 74 |
| Control example 9 | Kidney yang deficiency | 30 | 19 | 1 | 60 | 28 | 21 | 1 | 56 |

As can be seen from Table 4, when the pre-immune composition was not contained, that is, before applying the medicine, the pre-immune composition was not applied to the corresponding sites, the corresponding sites were scrubbed only with clear water, and other prescriptions remained the same, the cure rate was still low under the condition that the treatment time was extended for two times (the treatment time in Table 3 was 10 days, and the treatment time in Table 4 was 2 weeks and 14 days). As can be seen from Table 3, the combined external medicine for treating prostatic hyperplasia provided by the present invention has a short treatment period and an improved cure rate, and the cure rate can reach 86% or more within 10 days.

What is claimed is:

1. A combined external medicine for treating prostate diseases, comprising:
    a pre-immune composition comprising a i26 immune egg powder and a noble bottle tree decoction;
    a lesion active composition comprising the i26 immune egg powder and a first medical decoction prepared from a first Chinese medical composition for treating prostate diseases; and
    a double rib active composition comprising the i26 immune egg powder and a second medical decoction prepared from a second Chinese medical composition for conditioning liver and kidney wherein
    the i26 immune egg powder and the noble bottle tree decoction of the pre-immune composition are in a weight ratio of 30-40:60-70;
    the i26 immune egg powder and the first Chinese medical composition of the lesion active composition are in a weight ratio of 30-40:60-70; and
    the i26 immune egg powder and the second Chinese medical composition of the double rib active composition are in a weight ratio of 30-40:60-70.

2. The composition of claim 1, wherein the second Chinese medical composition for conditioning liver and kidney comprises a first ingredient, a second ingredient, or a third ingredient, wherein the first ingredient comprises:
    15-30 parts by weight of radix rehmanniae, 15-30 parts by weight of rehmanniae vaporata, or 15-30 parts by weight of a mixture of radix rehmanniae and rehmanniae vaporata in a weight ratio of 1:1;
    10-20 parts by weight of fructus corni;
    15-30 parts by weight of rhizoma dioscoreae;
    6-12 parts by weight of cortex moutan; 6-12 parts by weight of poria cocos;
    6-12 parts by weight of rhizoma alismatis;
    10-20 parts by weight of cuscuta chinensis lam;
    10-20 parts by weight of semen astragali complanati; and
    10-20 parts by weight of rhizoma polygonati; and
    the second ingredient comprises:
    15-30 parts by weight of radix rehmanniae, 15-30 parts by weight of rehmanniae vaporata, or 15-30 parts by weight of a mixture of radix rehmanniae and rehmanniae vaporata in a weight ratio of 1:1;
    10-20 parts by weight of fructus corni;
    15-30 parts by weight of rhizoma dioscoreae;
    6-12 parts by weight of cortex moutan;
    6-12 parts by weight of poria cocos;
    6-12 parts by weight of rhizoma alismatis;
    15-30 parts by weight of rhizoma anemarrhenae; and
    15-30 parts by weight of cortex phellodendri; and
    the third ingredient comprises:
        15-30 parts by weight of radix rehmanniae, 15-30 parts by weight of rehmanniae vaporata, or 15-30 parts by weight of a mixture of radix rehmanniae and rehmanniae vaporata in a weight ratio of 1:1;
    10-20 parts by weight of fructus corni;
    15-30 parts by weight of rhizoma dioscoreae;
    6-12 parts by weight of cortex moutan;
    6-12 parts by weight of poria cocos;
    6-12 parts by weight of rhizoma alismatis;
    10-20 parts by weight of rhizoma polygonati;
    10-20 parts by weight of morindae officinalis;
    10-30 parts by weight of herba epimedii;
    10-30 parts by weight of cortex cinnamomi; and
    10-30 parts by weight of radix paeoniae alba.

3. The composition of claim 2, wherein the first Chinese medical composition comprises:
    15-30 parts by weight of leech;
    20-40 parts by weight of earthworm;
    15-30 parts by weight of eupolyphaga;
    20-50 parts by weight of fructus foeniculi;
    20-40 parts by weight of concha ostreae;
    10-20 parts by weight of pangolin scales;
    20-40 parts by weight of carapax trionycis;
    15-30 parts by weight of radix achyranthis bidentatae;
    20-40 parts by weight of rhizoma sparganii;
    20-40 parts by weight of rhizoma curcumae;
    15-30 parts by weight of radix notoginseng;
    20-40 parts by weight of litchi chinensis sonn,
    20-60 parts by weight of caulis spatholobi;
    20-40 parts by weight of chinese honeylocust spine;
    20-40 parts by weight of dandelion;
    15-30 parts by weight of myrrh;
    15-30 parts by weight of frankincense;
    15-30 parts by weight of acacia catechu;
    20-40 parts by weight of semen plantaginis;
    20-40 parts by weight of hedyotis diffusa;
    20-40 parts by weight of tangerine seed;
    20-40 parts by weight of cyrtomium fortunei;
    15-30 parts by weight of rhizoma chuanxiong; and
    15-30 parts by weight of prunella vulgaris.

4. The composition of claim 2, wherein the first Chinese medical composition comprises:
    10-30 parts by weight of cortex phellodendri;
    10-30 parts by weight of rhizoma anemarrhenae;
    5-15 parts by weight of pangolin scales;
    10-20 parts by weight of carapax trionycis;
    10-30 parts by weight of concha ostreae;
    10-30 parts by weight of radix achyranthis bidentatae;
    20-50 parts by weight of lysimachia christinae hance;
    10-30 parts by weight of fructus crataegi;
    10-30 parts by weight of rhizoma curcumae;
    10-30 parts by weight of semen plantaginis;
    10-40 parts by weight of caulis spatholobi;
    20-40 parts by weight of herba leonuri;
    10-30 parts by weight of rheum officinale;
    10-30 parts by weight of chinese honeylocust spine;
    10-30 parts by weight of acacia catechu;
    10-30 parts by weight of leech;
    10-30 parts by weight of lumbricus;
    10-30 parts by weight of eupolyphaga;
    15-50 parts by weight of largehead atractylodes rhizome;
    10-30 parts by weight of rhizoma chuanxiong; and
    10-30 parts by weight of prunella vulgaris.

5. A method for treating prostate diseases by administering the composition of claim 1, comprising:
   applying the pre-immune composition on skin of lesion part and skin of the left and right ribs;
   waiting for 5-10 minutes;
   applying the lesion active composition and the double rib active composition on the skin of the lesion part and skin of the left and right ribs respectively; and
   airing for 10-40 minutes.

6. The method of claim 5, wherein the composition of claim 1 is used in the morning and in the evening.

7. The method of claim 5, wherein the lesion part is skin of perineum and testis.

\* \* \* \* \*